United States Patent [19]
Heuscher et al.

[11] Patent Number: 6,154,516
[45] Date of Patent: Nov. 28, 2000

[54] CARDIAC CT SYSTEM

[75] Inventors: Dominic Heuscher, Aurora; Shalabh Chandra; Raj Shekhar, both of Mayfield Heights; Dave Hoffmeyer, Concord, all of Ohio

[73] Assignee: Picker International, Inc., Highland Heights, Ohio

[21] Appl. No.: 09/157,028

[22] Filed: Sep. 18, 1998

Related U.S. Application Data

[60] Provisional application No. 60/099,234, Aug. 4, 1998.

[51] Int. Cl.$^7$ ............................. G01N 23/083; A61B 6/03
[52] U.S. Cl. .............................................. 378/15; 378/901
[58] Field of Search .................... 378/4, 15, 901, 378/208

[56] References Cited

U.S. PATENT DOCUMENTS

| | | | |
|---|---|---|---|
| 4,573,179 | 2/1986 | Rutt | 378/10 |
| 5,262,946 | 11/1993 | Heuscher | 378/15 |
| 5,383,231 | 1/1995 | Yamagishi | 378/15 |
| 5,396,418 | 3/1995 | Heuscher | 378/15 |
| 5,485,493 | 1/1996 | Heuscher et al. | 378/15 |
| 5,544,212 | 8/1996 | Heuscher | 378/15 |
| 5,612,985 | 3/1997 | Toki et al. | 378/4 |
| 5,751,782 | 5/1998 | Yoshitome | 378/98.5 |
| 5,832,051 | 11/1998 | Lutz | 378/8 |

FOREIGN PATENT DOCUMENTS

WO 98/32371  7/1998  WIPO .

OTHER PUBLICATIONS

J. Shemesh, et al., "Coronary Calcium Measurements by Double Helical Computed Tomography," *Investigative Radiology*, vol. 32, No. 9, pp. 503–506, 1997.

J. Shemesh, et al., "Coronary Artery Calcification in Women with Syndrome X: Usefulness of Double–Helical CT for Detection," *Cardiac Radiology*, 1997; vol. 205; pp. 697–700.

C. E. Woodhouse, et al., "Coronary Arteries: Retrospective Cardiac Gating Technique to Reduce Cardiac Motion Artifact at Spiral CT," Journal Article Abstract, *Radiology*, Aug. 1997, vol. 204, pp. 566–569.

T. Mochizuki, et al., "CT–Ventriculagraphy: A New Application of the Helical CT," Journal Article English Abstract, *Nippon Igaku Hoshasen Gakkai Zasshi*, Aug. 1997, vol. 57, pp. 605–607.

(List continued on next page.)

*Primary Examiner*—Donald Hajec
*Assistant Examiner*—Drew A. Dunn
*Attorney, Agent, or Firm*—Fay, Sharpe, Fagan, Minnich & McKee, LLP

[57] ABSTRACT

A cardiac gated spiral CT scanner (10) has a source of penetrating radiation (20) arranged for rotation about an examination region (14) having a central axis extending in a z direction. The source (20) emits a beam of radiation (22) that passes through the examination region (14) as the source (20) rotates. A patient support (30) holds a patient within the examination region (14) and translates the patient through the examination region (14) in the z direction while this source (20) is rotated such that the source (20) follows a helical path relative to the patient. A control processor (90) implements a patient-specific scan protocol in response to measured patient characteristics (for example, the patient's heart rate, the patient's breath hold time, and/or the range of coverage in the z direction based on the patient's anatomy) and scanner characteristics (for example, the number of detector rings, and/or the scan rate). Radiation detectors (40) are arranged to receive radiation from the source (20) after it has traversed the examination region (14). An ECG monitor (80) acquires ECG data from the patient. The ECG data is used to correlate phases of the patient's heart with data collected by the radiation detectors (40). An image reconstruction processor (60) reconstructs image representations of the patient based on data received from the radiation detectors (40) and ECG monitor (80). A human viewable display (70) selectively displays the image representations for assessing cardiac function.

21 Claims, 2 Drawing Sheets

OTHER PUBLICATIONS

F. Kimura, "A New Helical CT Approach with ECG Gated Reconstruction," Journal Article English Abstract, *Nippon Igaku Hoshasen Gakkai Zasshi*, Mar. 1997, vol. 57, pp. 217–219.

S. Achenbach, et al., "Curved Multiplanar Reconstructions for the Evaluation of Contrast–Enhanced Electron Beam CT of the Coronary Arteries", *American Journal of Roentgenology*, Apr. 1998, vol. 170, pp. 895–899.

Y. Arad, et al., "Correlations Between Vascular Calcification and Atherosclerosis: A Comparative Electron Beam CT Study of the Coronary and Carotid Arteries," *Journal of Computer Assisted Tomography*, 1998, vol. 22, No. 2, pp. 207–211.

L. S. Broderick, et al., Measurement of Coronary Artery Calcium with Dual–Slice Helical CT Compared with Coronary Angiography, *American Journal of Roentgenology*, Aug. 1996, vol. 167, pp. 439–444.

"GE Medical Systems Bolsters Cardiology with Imatron Deal, CAC Scoring Package," *Medical Imaging News*, Jun. 26, 1998, vol. 7, No. 25, pp. 1.

"Subsecond Cardio CT Software Package from Siemens Reduces Motion Artifacts, Improves Heart, Lung Images," *HEADSUP*, PR Newswire, Jun. 5, 1998.

C. E. Woodhouse, et al., "Detection of Coronary Calcification Using Retrospective Cardiac Gating of Spiral CT Scans."

EP Search Report, EP 99306966, Nov. 22, 1999.

CARDIAC CT SYSTEM

This application claims the benefit of U.S. Provisional Application No. 60/099,234, filed Aug. 4, 1998.

BACKGROUND OF THE INVENTION

The present invention relates to the art of diagnostic computed tomography (CT) imaging. It finds particular application in conjunction with cardiac gated spiral CT scanners, and will be described with particular reference thereto. However, it is to be appreciated that the present invention is also amenable to other like applications.

In typical spiral or helical CT scanning, an x-ray source or tube emits a fan beam of radiation as it rotates continuously around an examination region as a patient support table moves therethrough at a constant, linear velocity. Detectors positioned across the examination region from the x-ray tube convert x-rays which traverse the patient into corresponding electronic data. The collected data effectively represents a helical path of constant pitch through the patient. The helical data is reconstructed into a volumetric image representation, typically a series of consecutive thin slice images of a region of interest of the patient. See for example, U.S. Pat. Nos. 5,544,212; 5,485,493; 5,262,946; and, 5,396,418; all commonly assigned and incorporated by reference herein.

Furthermore, a number of methods are aimed at reconstructing cardiac images with reduced motion artifacts. For example: a prospective electrocardiogram (ECG) gated method with axial slice CT acquisition has been used to reconstruct cardiac images, as shown in U.S. Pat. No. 5,751,782 to Yoshitome; a retrospective ECG-gated CT data acquisition and reconstruction technique using spiral CT is also known; a prospective ECG-gated technique with spiral CT data acquisition for imaging only the diastolic phase of the heart is known; and, a prospective ECG-gated technique is known which employs a scan time of 100 ms/slice in an electron beam CT (EBCT) scanner such as the one described in U.S. Pat. No. 4,573,179 to Rutt. However, the above techniques have failed to provide a generalized scheme for cardiac reconstruction of any selected cardiac phase for various heart rates and/or different gantry speeds and configurations. In addition, the above techniques suffer from various drawbacks and are therefore less than ideal in certain aspects for diagnostic cardiac imaging.

For example, one drawback of the technique employed in U.S. Pat. No. 5,751,782 and other such cardiac gated axial slice systems is that they use multiple rotations for reconstructing a single slice, and hence, have a longer scan time. A disadvantage of retrospective ECG-gated CT data reconstruction is that processor resources and time is consumed in the processing of too many images. Additionally, the prior art techniques do not consider advantageous multi-ring scanner configurations. The aforementioned prospective ECG-gated technique with spiral CT acquisition is less than ideal in that it is limited to a given phase of the heart and does not demonstrate the detector configuration, scanner speed, and imaging protocol best for removing motion artifacts.

Use of EBCT imaging in diagnostic cardiac applications also has certain drawbacks. First of all, it is primarily a research tool and it is not as widely available for clinical applications as conventional spiral CT scanners. In addition, EBCT scanners are generally much more expensive. Often, EBCT scanners have poor image quality and their z-axis resolution limits usefulness.

The present invention contemplates a new and improved cardiac gated spiral CT imaging apparatus and technique which overcomes the above-referenced problems and others.

SUMMARY OF THE INVENTION

In accordance with one aspect of the present invention, a cardiac gated spiral CT scanner includes a source of penetrating radiation arranged for rotation about an examination region having a central axis extending in a z direction. The source emits a beam of radiation that passes through the examination region as the source rotates. A patient support holds a patient being examined at least partially within the examination region and translates the patient through the examination region in the z direction while the source is rotated such that the source follows a helical path relative to the patient. A control processor implements a patient-specific scan protocol in response to measured patient characteristics and scanner characteristics. Radiation detectors are arranged to receive radiation emitted from the source after it has traversed the examination region. An ECG monitor acquires ECG data from the patient. The ECG data is used to accurately correlate phases of the patient's heart with data collected by the radiation detectors. An image reconstruction processor reconstructs image representations of the patient based on data received from the radiation detectors and ECG monitor. Ultimately, a human viewable display selectively displays the image representations for assessing cardiac function.

In accordance with a more limited aspect of the present invention, the measured patient characteristics include one or more of those selected from a group consisting of average patient heart rate, patient breath hold time, and range of scan coverage in the z direction based on patient anatomy.

In accordance with a more limited aspect of the present invention, the control processor accesses a look up table in response to the measured patient characteristics and scanner characteristics. The look up table contains the scan protocols.

In accordance with a more limited aspect of the present invention, the scan protocol selected sets a pitch for the helical path followed by the source and sets an image slice thickness, such that (i) the patient's average heart rate, (ii) the patient's breath hold time, and (iii) a range of scan coverage in the z direction are accommodated while ensuring that neighboring image slices are at least contiguous in the z direction.

In accordance with a more limited aspect of the present invention, there are one or more sets of radiation detectors and the one or more sets are arranged such that they reside in separate corresponding parallel planes. The planes are displaced from one another in the z direction.

In accordance with a more limited aspect of the present invention, the scan protocol selected is dependent on how many sets of radiation detectors there are.

In accordance with a more limited aspect of the present invention, the source continuously emits the beam of radiation that passes through the examination region during an entire imaging scan.

In accordance with a more limited aspect of the present invention, the image representation is of the patient's heart and associated vasculature in a selected phase.

In accordance with a more limited aspect of the present invention, the image representation is three-dimensional.

In accordance with another aspect of the present invention, a method for cardiac gated spiral CT imaging is provided. The method includes assessing a breath hold time for a patient, measuring an average heart rate of the patient, and determining a range of scan coverage. Next, based on results from the initial steps, a patient-specific scan protocol is selected. In accordance with the selected scan protocol, a spiral CT scan of the patient is performed while collecting ECG data from the patient. The ECG data is used to correlate phases of the patient's heart with x-ray data collected via the spiral CT scan. Ultimately, an image representation of a region of interest of the patient at a point in time corresponding to a selected phase of the patient's heart is reconstructed from the x-ray data collected.

In accordance with a more limited aspect of the present invention, reconstruction takes place in either or both of a prospective manner while x-ray data is being collected and a retrospective manner after completing collection of the x-ray data.

In accordance with a more limited aspect of the present invention, the range of scan coverage is determined by performing a pilot scan of the region of interest of the patient.

In accordance with a more limited aspect of the present invention, the selected scan protocol determines (i) a pitch for a spiral path traveled by an x-ray source relative to the patient during the spiral CT scan and (ii) an image slice thickness, such that neighboring image slices are at least contiguous along a direction of the pitch.

In accordance with a more limited aspect of the present invention, the image representation is three-dimensional.

In accordance with a more limited aspect of the present invention, the region of interest includes the patient's heart and associated vasculature.

In accordance with a more limited aspect of the present invention, the method further includes three-dimensionally measuring and scoring coronary calcification.

In accordance with a more limited aspect of the present invention, the method further includes measuring and monitoring cardiac structure and function three-dimensionally.

In accordance with a more limited aspect of the present invention, the scan protocol is adjusted during the spiral CT scan in response to changes in the patient's heart rate.

One advantage of the present invention is that it provides a versatile and selectable protocol for cardiac gated spiral CT imaging which is patient-specific.

Another advantage of the present invention is improved cardiac images with reduced motion artifacts.

Yet another advantage of the present invention is reduced scan times as compared to gated axial slice CT and prospective single cardiac phase spiral CT.

One more advantage of the present invention is that resolution along the longitudinal axis of the scan is maintained for improved three-dimensional imaging and diagnostic evaluations of the heart and associated vasculature.

Another advantage of the present invention is that any selected phase of the heart may be imaged.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
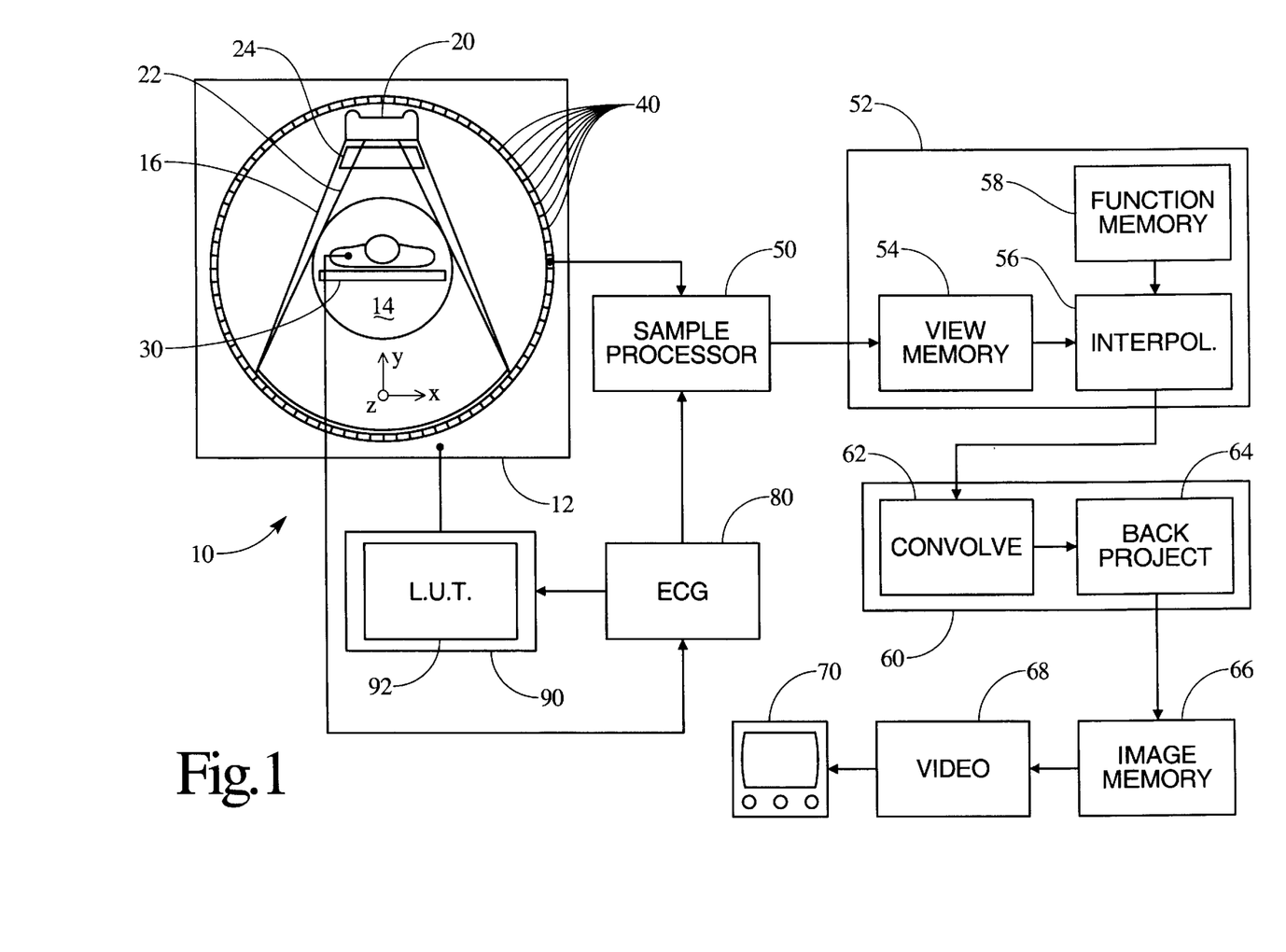
FIG. 1 is a diagrammatic illustration of a cardiac gated spiral CT scanner in accordance with aspects of the present invention; and, FIG. 2 is a flow chart illustrating a cardiac rates spiral CT imaging technique in accordance with aspects of the present invention.

With reference to FIG. 1, a cardiac gated spiral CT scanner 10 includes a stationary gantry portion 12 which defines an examination region 14 having a central axis extending in the z direction. A rotating gantry portion 16 is mounted on the stationary gantry portion 12 for rotation about the examination region 14. A penetrating radiation source 20, such as an x-ray tube, is arranged on the rotating gantry portion 16 such that a beam of radiation 22 passes through the examination region 14 as the rotating gantry portion 16 rotates. A collimator and shutter assembly 24 forms the beam of radiation 22 into a thin fan-shaped beam and selectively gates the beam 22 on and off. Alternately, the fan-shaped radiation beam 22 may also be gated on and off electronically at the source 20.

A patient support 30, such as a couch or the like, suspends or otherwise holds a patient being examined or imaged at least partially within the examination region 14. Moreover, as the rotating gantry porion 16 rotates, the support 30, and consequently the patient thereon, are translated in the z direction. In this manner, the source 20 follows a helical path relative to the patient.

In the illustrated fourth generation scanner, a ring of radiation detectors 40 are mounted peripherally around the examination region 14 on the stationary gantry portion 12. Alternately, a third generation scanner is employed with the radiation detectors 40 mounted on the rotating gantry porion 16 on a side of the examination region 14 opposite the source 20 such that they span the arc defined by the fan-shaped beam 22. Regardless of the configuration, the radiation detectors 40 are arranged to receive the radiation emitted from the source 20 after it has traversed the examination region 14.

In an alternate preferred embodiment, there are multiple sets of radiation detectors 40 residing in separate corresponding parallel planes. The planes a displaced from one another in the z direction. In a fourth generation scanner, this configuration is achieved by having multiple rings (each ring displaced from one another in the z direction) of radiation detectors 40 mounted peripherally around the examination region 14 on the stationary gantry portion 12. In a third generation scanner, similarly, multiple arcs of radiation detectors 40 are employed. When multi-ring or multi-arc configurations are employed, the beam 22 employed is a cone beam arranged to diverge in two dimensions.

In a source fan geometry, an arc of detectors which span the radiation emanating from the source 20 are sampled concurrently at short time intervals as the source 20 rotates behind the examination region 14 to generate a source fan view. In a detector fan geometry, the detectors are sampled a multiplicity of times as the source 20 rotates behind the examination region 14 to generate a detector fan view. The path between the source 20 and each of the radiation detectors 40 is denoted as a ray.

The radiation detectors 40 convert the detected radiation into electronic data. That is to say, each of the radiation detectors produces an output signal which is proportional to an intensity of received radiation. Optionally, a reference detector may detect radiation which has not traversed the examination region 14. A difference between the magnitude of radiation received by the reference detector and each radiation detector 40 provides an indication of the amount of radiation attenuation along a corresponding ray of a sampled fan of radiation.

In detector fan geometry, each view or data line represents a fan of rays having its apex at one of the radiation detectors 40 collected over a short period of time as the source 20 rotates behind the examination region 14 from the detector. In source fan geometry, each view or data line represents a fan of rays having an apex at the source 20 collected by concurrent sampling of all detectors. Contiguous fan views which span 180° plus the angle of the fan constitute a complete set of data for reconstruction into an image slice.

A sampling processor 50 receives sampled data from the radiation detectors 40. The sampling processor 50 optionally shuffles the data to transform it from a detector fan geometry to a source fan geometry or vice versa and performs a ripple filtering operation before passing the data on. The sampled fan views correspond to each angular position of the source 20 around the examination region 14 for each of a multiplicity of rotations. The apexes of the fan views are disposed along the helical path and are defined by an angular orientation $\phi$ around the imaged volume and by a longitudinal position in the z direction along the imaged volume. Data or rays within each fan are further identified by their angle $\alpha$ within the fan.

A view processor 52 converts the spiral sampled views into planar data sets. The view processor includes a memory 54 which stores the spiral sampled views. An integrating interpolator 56 integrates corresponding rays of a preselected number of contiguous sets of spiral data with a filter or interpolation function retrieved from a memory 58 to produce parallel axial slices. The memory 58 stores a plurality of filter or interpolation functions for integrating different numbers of spiral fan views. The more views that are combined, the thicker the corresponding image slice.

Thereafter, the combined set of data is conveyed to an image reconstruction processor 60. The image reconstruction processor 60 processes the data from the view processor 52 and backprojects it into an image memory 66. More specifically, the image reconstruction processor 60 performs mathematical manipulations which convolve each data set with an appropriate filter or convolution function for the view format. The image reconstruction processor 60 of the preferred embodiment includes a convolver 62 which convolves the thick slice interpolated data sets and a backprojector 64. The backprojector 64 backprojects the convolved data sets into the image memory 66. Ultimately, a video processor 68 selectively retrieves slices, projections, three-dimensional (3D) renderings, and other image information from the image memory 66 and appropriately formats an image representation for display on a human viewable display 70, such as a video monitor or the like.

Via leads attached to the patient, an ECG monitor 80 (preferably digital) acquires ECG data from the patient. The ECG data is used to accurately correlate phases of the patient's heart with data collected by the radiation detectors 40. More specifically, in a preferred embodiment, the sampling processor 50 tags sampled data views with the ECG data.

In operation, a control processor 90 implements a patient-specific scan protocol in response to measured patient characteristics and scanner characteristics. More specifically, in a preferred embodiment, the control processor accesses a look up table 92 which contains various scan protocols. The look up table 92 is accessed based on the following measured patient characteristics: the patient's assessed breath hold time (i.e. how long the patient can hold his breath, which, for a single breath hold scan, limits the total scan time); the patient's average or mean heart rate (obtained from the ECG monitor 80); and, the range of scan coverage in the z direction (the range of scan coverage in the z direction is chosen based on the particular patient's anatomy and the desired region of interest to be imaged, in a preferred embodiment the region of interest is the patient's heart and associated vasculature).

Figure 2:
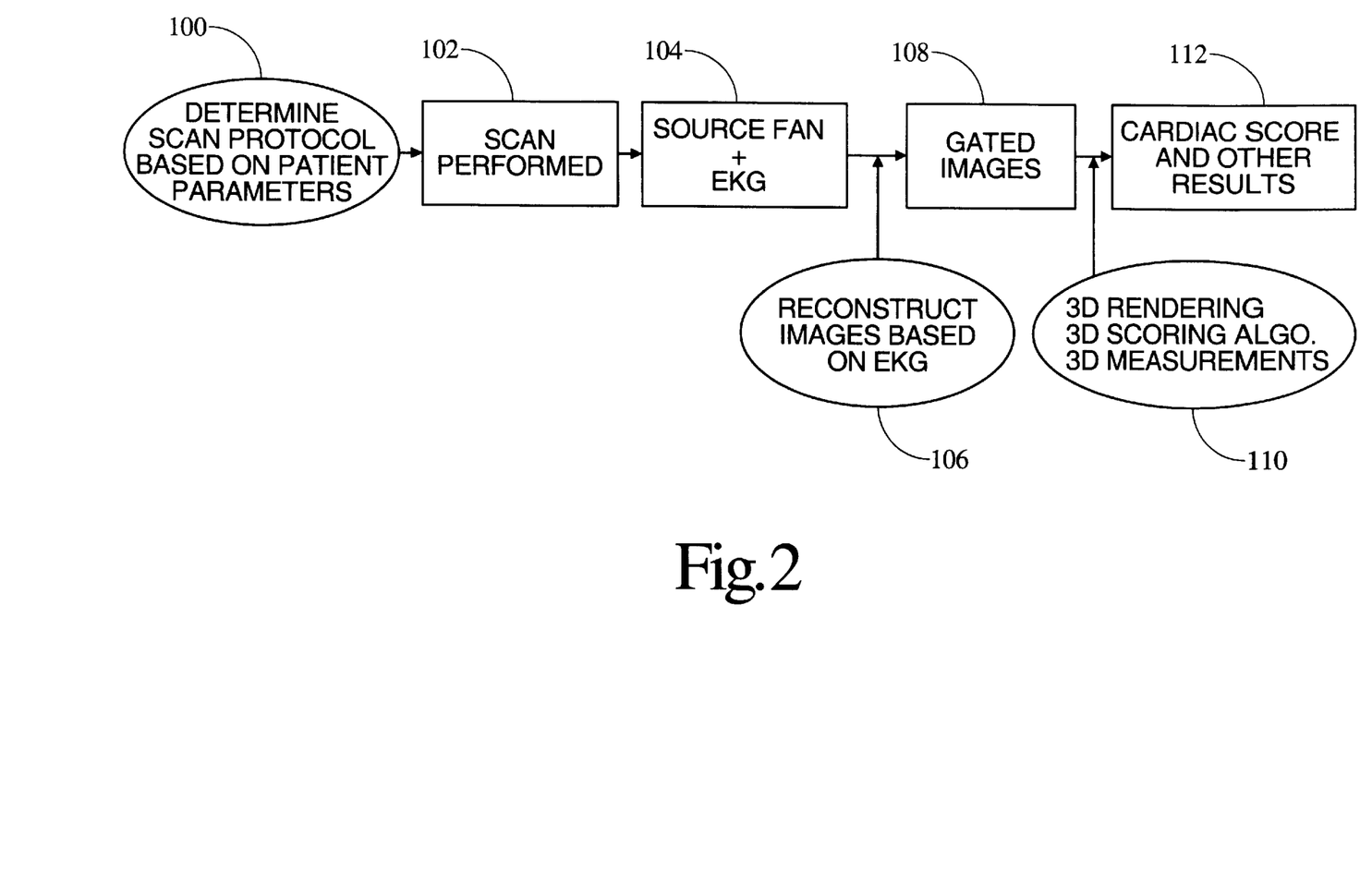

With reference to FIG. 2 and continuing reference to FIG. 1, a method of cardiac gated spiral CT imaging in accordance with a preferred embodiment of the present invention is set forth in the illustrated flow chart. The parameters used in the following description are as follows:

the scan rate (sr) (e.g. 60, 90, 120, or 300 rpm) is the rate of rotation of the rotating gantry portion 16;

the pitch (p) (e.g. 0 to 8 mm) is the pitch of the helical path followed by the source 20 and it is determined by the rate at which the patient support 30 translates the patient through the examination region 14;

the detector ring width (d) (e.g. 1.3 or 4 mm) is the dimension of the radiation detectors 40 in the z direction;

effective reconstructed slice thickness (est) is the effective image slice thickness in the z direction;

rings reconstructed (rr) (e.g. 1, 2, or 3);

the number of detector rings (nr) (e.g. 1, 2, 3, 5, or 9) takes into account multi-ring or multi-arc scanner configurations;

the heart rate (hr) (e.g. 40–180 beats per minute (bpm)) is measured by the ECG monitor 80;

the total scan time (T) (e.g. 20–40 seconds) is limited by the assessed patient breath hold time in single breath hold scans;

temporal resolution ($\Delta t$) (e.g. 250 ms);

the total scan coverage (C) (e.g. 6–32 cm) in the z direction is determined by the patient's anatomy and the desire region of interest;

a minimum applicable heart rate (hrmin) for a desired coverage; and, the maximum patient support travel in the z direction measured in millimeters per heart beat (mmpb).

The first step 100 is to select or determine the scan protocol based on patient parameters. The patient holds his breath and his breath-hold time is assessed. Via the ECG monitor 80, the heart rate of the patient is measured over a period of time and the average or mean heart rate for the patient is calculated. In a preferred embodiment, the average or mean heart rate is measured while the patient is holding his breath to mimic upcoming imaging scan conditions. A pilot scan is performed to determine the scan range in the z direction. That is to say, the pilot scan roughly images the patient's anatomy so that the range of coverage in the z direction which contains the desired region of interest is readily discernable. Again, in a preferred embodiment, this takes place simultaneously with the breath hold. Based on these patient parameters and the particular scanner configuration employed, the control processor 90 selects a scan protocol from the look up table 92. In this manner, the scan protocol is customized (i.e., the pitch, slice thickness, etc. are set to accommodate the patient parameters and scanner configuration) for each patient. In a preferred embodiment, the protocol selected operates to maximize resolution in the z direction by maintaining a continuous set of image slice data in the z direction. That is to say, the pitch and slice thickness are set such that neighboring slices either overlap or are at least contiguous. Table 1 provided below illustrates exemplary protocols for various patient parameters and scanner configurations (see below for detailed derivation of table parameters).

Sample Cardiac Ct configurations and Protocols for 20 seconds of Breath-hold

TABLE 1

| Scanner Configuration nr × d | Reconstruction Mode rr (# rings) | Scan Rate sr (rpm) | Temporal Resolution Δt (msec) | Eff. Slice Thickness est (mm) | Coverage C (cm) | Heart Rate hrmin (bpm) | Pitch p (mm) |
|---|---|---|---|---|---|---|---|
| 1 × 4 mm spiral | 1 | 60 | 500–550 | 4.0 | 6 | 45+ | 3 |
| 3 × 4 mm spiral | 1 | 90 | 330–360 | 4.2 | 16 | 40+ | 5.3 |
| 5 × 1.3 mm spiral | 1 | 120 | 250–270 | 1.9 | 12 | 54+ | 3 |
| 100 × 1.3 mm 0-pitch | 1 | 300 | 80–110 | 1.3 | 13 | (all) | 0 |

The next step 102 is to run the imaging spiral CT scan in accordance with the selected protocol. The ECG monitor 80 is used to acquire ECG data simultaneously with the spiral CT scan. In one embodiment, prior to the scan, a calibration is performed to account for any latency between delivery of the ECG data and the data collected from the radiation detectors 40. As illustrated at step 104, the sampling processor 50 tags each sampled fan view of data with the ECG amplitude and it is saved as part of every fan view such that various phases of the heart are accurately correlated to the view data. The source of penetrating radiation 20 stays on throughout the imaging scan to enable reconstruction of any selected phase of the heart.

At step 106, image reconstruction of planar slices takes place in accordance with the ECG data to produce cardiac gated images 108. The reconstructed image slices correspond to a point in time when the heart is in a selected phase. In a preferred embodiment, over all image continuity is maintained by reconstructing contiguous image slices from contiguous heart beats. In any event, the interpolated axial slices that make up the volumetric image are centered on transverse axial planes located along the helical path where the phase of the heart is at the same position in its biological cycle as predicted from the ECG data. That is to say, the interpolator 56 centers the interpolation filter function retrieved from the memory 58 at that point on the helical path. In this manner, the technique is prospective in nature and the image reconstruction takes place while data continues to be collected from the radiation detectors 40. In addition however, being that the source 20 remains on throughout the imaging scan and a complete helical set of data is collected, optionally different images (corresponding to different points in the cardiac cycle) are reconstructed retrospectively by selecting a set of centering points along the helical path where the heart is in a different phase.

At step 110, the gated images from 108 are employed for 3D rendering and other clinical applications (discussed later herein) which measure and monitor cardiac structure and function three-dimensionally to reach a diagnosis or other result 112.

The scan protocols associated with a particular scanner configuration are chosen in accordance with calculations using the parameters set forth in the list above. Moreover, the scan protocols are applicable to a number of variable scanner configurations.

In one preferred embodiment, the scanner configuration is not spiral. That is to say, the pitch of the helical path is zero such that axial slice data is collected. These 0-pitch scans are limited in z direction coverage by the number of detector rings used in the scan. With nr detector rings, nr axial images slices are reconstructed along the z direction, and the coverage is given by the following:

$$C = nr \cdot d \quad (1).$$

In operation, the ECG data is used to reconstruct and view the images slices simultaneously at one or more selected phase of the heart cycle. Optionally, these gated images are averaged over several heart cycles to improve contrast resolution, or compared over time, at the risk of patient movement, in which case it is desirable to have the patient hold his breath.

In another preferred embodiment, the scanner configuration is spiral. The objective in this case is to scan as much of the heart as possible (i.e., up to at least 20 cm), while maintaining good z direction resolution along the scanned volume for a selected phase of the heart cycle. Preferably, this scan is performed within a single breath hold (e.g., 20 to 40 seconds). Knowing the average heart rate is valuable in choosing the right scan protocol and method of reconstruction. To maintain adequate z direction resolution across the scanned volume, the following condition is met:

$$mmpb < (nr - rr + 1) \cdot d \quad (2).$$

In other words, the distance in mm of couch travel within one heart beat (mmpb) should be less than the distance between the first and last subset of rr out of nr rings (nr−rr+1) used to simultaneously reconstruct cardiac images at a selected phase of the heart cycle. For example, in a single-ring scan, nr=rr=1, or mmpb<d; and, in a five-ring scan using each ring separately to reconstruct image slices along the spiral, mmpb<(5−1+)·d=5·d. Then, for a given pitch p and scan rate sr, this provides a minimum heart rate supported by the cardiac reconstruction as follows:

$$hrmin = sr \cdot p / (nr - rr + 1) \cdot d \quad (3).$$

For a given total scan time T, the corresponding coverage C in cm is given by the following:

$$C = sr \cdot T \cdot p / 600 \quad (4).$$

Using these relationships between heart rate, scan rate, and coverage, the following holds for a single-ring scan and a multi-ring scan. Consider for example, a single-ring scan with a 4 mm detector width (d). Coverage in this case ranges from 6 to 16 cm for heart rates from 45–120 bpm. For a multi-ring scan, with a 3×4 configuration and a scan speed of 60 rpm using a dual-ring (rr=2) reconstruction, the coverage is as much as 32 cm in 20 seconds, as long as the heart rate is greater than 60 bpm. As these numbers demonstrate, coverage and resolution is improved considerably by using a multi-ring scanner configuration.

Additionally, temporal resolution is maximized by using 180-plus-fan reconstruction weighting functions (i.e., those interpolation or filter functions stored in the memory 58) whose FWHM values are anywhere from 0.4 to 0.55 of one revolution while still maintaining unity-sum weighting over 180 degrees. In this case, the temporal resolution is given by the following:

$$\Delta t = (0.4 \text{ to } 0.55) \cdot 60/sr \qquad (5).$$

In one preferred embodiment, 0.4 revolution FWHM is achieved using a single-side-lobe higher order weighting function, which improves temporal resolution but also increases the noise in the reconstruction. Parallel beam reconstruction over 180 degrees with uniform weighting achieves a FWHM of 0.5 revolution. The standard spiral interpolator (smooth triangle with 0.9 peak value) achieves a FWHM of 0.55 revolution. Moreover, in response to the particular phase of the heart being imaged, different weighting functions are selected from the memory 58 which are most appropriate for bringing out or highlighting that phase. That is to say, different functions are used to produce higher quality cardiac images based on the phase of the heart being reconstructed.

Optionally, the weighting function is selected from the memory 58 such that it employs angular segments of spiral data corresponding to portions of neighboring cardiac cycles to achieve higher temporal resolution. For this technique, the rotational gantry speed is selected based on the average heart rate to ensure that the aforementioned angular segments are minimally overlapping.

The cardiac gated spiral CT scanner and imaging techniques of the present invention, while not limited thereto, are particularly well suited to diagnostic 3D visualization and imaging of the heart and associated vasculature. In one preferred embodiment, the cardiac images are used to quantify calcifications. The calcification scoring is more accurate for gated images than ungated ones since the gated images have less motion artifacts. The selection of appropriate patient-specific scanning protocols also leads to uniform and continuous resolution in the z direction. Because of the uniform and continuous z direction resolution: (a) there is a very low probability that coronary calcification is missed; and, (b) the heart is reconstructed in 3D and, hence, a more accurate cardiac scoring algorithm base on 3D measurements is performed.

Another clinical application is the assessment of the coronary arteries from images reconstructed as proposed in this invention following intravenous injection of a radio-opaque dye. A CT-based coronary screening technique is virtually non-invasive and it may provide the same diagnostic information as provided by coronary angiography. Hence, the desired diagnostic information can be acquired non-invasively for initial screening purposes. Additionally, with volume images, the flexibility to view and assess the arteries from any angle in three dimensions is possible. Angiography, on the other hand, permits only a limited number of two dimensional projection views.

Moreover, in another preferred embodiment, applying the principles of continuous CT, functional imaging of the heart is performed. A bolus of contrast is tracked over time for the same phase of the heart using 0-pitch scanning. This gives insight into various flow-related heart abnormalities. In yet another preferred embodiment, comparison of the heart anatomy at various phases of the heart is performed. A segmentation and measurement package accurately yields clinically significant quantities such as end-diastolic volume, stroke volume, ejection fraction, and the dynamics of ventricular wall motion.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A CT scanner comprising:
   irradiating means and an examination region having a central axis extending in a z direction, said irradiating means emitting a beam of radiation that passes through the examination region as the irradiating means;
   follows a spiral path relative to a patient positioned in the examination region;
   detection means arranged to receive radiation emitted from the irradiating means after it has traversed the examination region;
   cardiac monitoring means for acquiring electrocardiogram data from the patient, said electrocardiogram data being used to accurately correlate phases of the patient's heart with data collected by the detection means;
   image reconstruction means for reconstructing image representations of the patient based on data received from the detection means and cardiac monitoring means;
   display means for selectively displaying the image representations in a human viewable format; and,
   control means for implementing a patient-specific scan protocol in response to measured patient characteristics and scanner characteristics, said patient-specific scan protocol determining a pitch of the spiral path and an image slice thickness such that neighboring image slices are at least contiguous along the z direction.

2. The CT scanner according to claim 1, wherein the measured patient characteristics include one or more of those selected from a group consisting of average patient heart rate, patient breath hold time, and range of scan coverage in the z direction based on patient anatomy.

3. A cardiac gated spiral CT scanner comprising:
   a source of penetrating radiation and an examination region having a central axis extending in a z direction, said source emitting a beam of radiation that passes through the examination region as the source follows a spiral path relative to a subject positioned within the examination region;
   radiation detectors arranged to receive radiation emitted from the source after it has traversed the examination region;
   an electrocardiogram monitor which acquires electrocardiogram data from the subject, said electrocardiogram data being used to accurately correlate phases of the subject's heart with data collected by the radiation detectors;
   an image reconstruction processor which reconstructs image representations of the subject based on data received from the radiation detectors and ECG monitor;
   a human viewable display which selectively displays the image representations; and,
   a control processor which implements a subject-specific scan protocol in response to measured subject characteristics and scanner characteristics;
   wherein the measured subject characteristics include one or more of those selected from a group consisting of average subject heart rate, subject breath hold time, and range of scan coverage in the z direction based on subject anatomy; and, wherein the control processor accesses a look up table in response to the measured subject characteristics and scanner characteristics, said look up table containing scan protocols.

4. A cardiac gated spiral CT scanner comprising:

a source of penetrating radiation and an examination region having a central axis extending in a z direction, said source emitting a beam of radiation that passes through the examination region as the source follows a spiral path relative to a patient positioned within the examination region;

radiation detectors arranged to receive radiation emitted from the source after it has traversed the examination region;

an electrocardiogram monitor which acquires electrocardiogram data from the patient, said electrocardiogram data being used to accurately correlate phases, of the patient's heart with data collected by the radiation detectors;

an image reconstruction processor which reconstructs image representations of the patient based on data received from the radiation detectors and ECG monitor;

a human viewable display which selectively displays the image representations; and, a control processor which implements a patient-specific scan protocol in response to measured patient characteristics and scanner characteristics;

wherein the measured patient characteristics include one or more of those selected from a group consisting of average patient heart rate, patient breath hold time, and range of scan coverage in the z direction based on patient anatomy; and, wherein the scan protocol selected sets a pitch for the spiral path followed and sets an image slice thickness, such that (i) the patient's average heart rate, (ii) the patient's breath hold time, and (iii) a range of scan coverage in the z direction are accommodated while ensuring that neighboring image slices are at least contiguous in the z direction.

5. The cardiac gated spiral CT scanner according to claim 4, wherein there are one or more sets of radiation detectors and the one or more sets are arranged such that they reside in separate corresponding parallel planes, said planes displaced from one another in the z direction.

6. The cardiac gated spiral CT scanner according to claim 5, wherein the scan protocol selected is dependent on how many sets of radiation detectors there are.

7. The cardiac gated spiral CT scanner according to claim 4, wherein the source continuously emits the beam of radiation that passes through the examination region during an entire imaging scan.

8. The cardiac gated spiral CT scanner according to claim 4, wherein the image representation is of the patient's heart and associated vasculature in a selected phase.

9. The cardiac gated spiral CT scanner according to claim 8, wherein the image representation is three-dimensional.

10. A method of cardiac gated spiral CT imaging comprising:

(a) assessing a breath hold time for a patient;
(b) measuring an average heart rate of the patient;
(c) determining a range of scan coverage;
(d) based on results from steps (a) through (c), selecting a patient-specific scan protocol;
(e) in accordance with the selected scan protocol, performing a spiral CT scan of the patient while collecting electrocardiogram data from the patient;
(f) using the electrocardiogram data to correlate phases of the patient's heart with x-ray data collected via the spiral CT scan; and,
(g) reconstructing from the x-ray data collected an image representation of a region of interest of the patient at a point in time corresponding to a selected phase of the patient's heart.

11. The method according to claim 10, wherein reconstruction takes place in either or both of a prospective manner while x-ray data is being collected and a retrospective manner after completing collection of the x-ray data.

12. The method according to claim 10, wherein the range of scan coverage is determined by performing a pilot scan of the region of interest of the patient.

13. The method according to claim 10, wherein the selected scan protocol determines (i) a pitch for a spiral path traveled by an x-ray source relative to the patient during the spiral CT scan and (ii) an image slice thickness, such that neighboring image slices are at least contiguous-along a direction of the pitch.

14. The method according to claim 10, wherein the image representation is three-dimensional.

15. The method according to claim 14, wherein the region of interest includes the patient's heart and associated vasculature.

16. The method according to claim 15, further comprising:

(h) three-dimensionally measuring and scoring coronary calcification.

17. The method according to claim 15, further comprising:

(h) measuring and monitoring cardiac structure and function three-dimensionally.

18. The method according to claim 10, wherein the scan protocol is adjusted during the spiral CT scan in response to changes in the patient's heart rate.

19. The method according to claim 10, further comprising:

selecting a weighting function used in interpolation of image slices from the x-ray data based on the selected phase of the patient's heart, at which point in time, the image representation is reconstructed.

20. The method according to claim 10, further comprising:

selecting a weighting function used in interpolation of image slices from the x-ray data based on the patient's heart rate.

21. In a cardiac gated spiral CT scanner including a stationary gantry portion defining an examination region having a central axis extending in a z direction; a rotating gantry portion arranged on the stationary gantry portion for rotation about the examination region; a source of penetrating radiation arranged on the rotating gantry portion for rotation therewith, said source emitting a beam of radiation that passes through the examination region as the source rotates; a patient support which holds a patient being examined at least partially within the examination region and translates the patient through the examination region in the z direction while the source is rotated such that the source follows a helical path relative to the patient; radiation detectors arranged to receive radiation emitted from the source after it has traversed the examination region; an electrocardiogram monitor which acquires electrocardiogram data from the patient, said electrocardiogram data being used to accurately correlate phases of the patient's heart with data collected by the radiation detectors; an image reconstruction processor which reconstructs image representations of the patient based on data received from the radiation detectors; and, a human viewable display which selectively displays the image representations; a scan control system comprising:

- a control processor which implements patient-specific scan protocols in response to the patient's average heart rate, scan coverage in the z direction, and the patient's breath hold time.

* * * * *